(12) United States Patent
Sommerfeld et al.

(10) Patent No.: US 8,455,024 B2
(45) Date of Patent: Jun. 4, 2013

(54) APPETITE SUPPRESSANT COMPOSITION

(75) Inventors: Audrey Sommerfeld, Hermosa Beach, CA (US); Steve Witherly, Valencia, CA (US)

(73) Assignee: ViSalus Holdings, LLC, Troy, MI (US)

( * ) Notice: Subject to any disclaimer, the term of this patent is extended or adjusted under 35 U.S.C. 154(b) by 416 days.

(21) Appl. No.: 12/252,871

(22) Filed: Oct. 16, 2008

(65) Prior Publication Data

US 2010/0098783 A1 Apr. 22, 2010

(51) Int. Cl.
*A61K 36/33* (2006.01)
*A61K 36/00* (2006.01)

(52) U.S. Cl.
USPC .......................................... 424/767; 424/725

(58) Field of Classification Search
None
See application file for complete search history.

(56) References Cited

U.S. PATENT DOCUMENTS

| | | | |
|---|---|---|---|
| 7,351,739 B2 | 4/2008 | Ho et al. | |
| 7,476,406 B1 * | 1/2009 | Smidt | 424/729 |
| 2002/0147152 A1 * | 10/2002 | Bell et al. | 514/21 |
| 2005/0276839 A1 | 12/2005 | Rifkin | |
| 2006/0051435 A1 | 3/2006 | Udell et al. | |
| 2006/0062859 A1 | 3/2006 | Blum et al. | |
| 2006/0078627 A1 * | 4/2006 | Maletto et al. | 424/638 |
| 2006/0127452 A1 | 6/2006 | Muller | |
| 2006/0204599 A1 * | 9/2006 | Wheat | 424/757 |
| 2006/0286183 A1 | 12/2006 | Gardiner et al. | |
| 2007/0116840 A1 * | 5/2007 | Prakash et al. | 426/548 |
| 2007/0117844 A1 * | 5/2007 | Morillo et al. | 514/317 |
| 2007/0237786 A1 | 10/2007 | Heuer | |
| 2007/0292501 A1 | 12/2007 | Udell | |
| 2008/0103111 A1 * | 5/2008 | Bieley | 514/52 |

FOREIGN PATENT DOCUMENTS

| | | | |
|---|---|---|---|
| JP | 2005239686 | * | 9/2005 |
| WO | 2007/132479 A1 | | 11/2007 |
| WO | 2007/143652 A2 | | 12/2007 |

OTHER PUBLICATIONS

Dr. Michael T. Murray—5-HTP—The natural plant extract that raises serotonin levels in the brain. http://www.5htp.com/, Sep. 16, 2008, 3 Pages.
5 Htp 100mg 30 Chewable Tables Mrm—http://www.shopping.com/xPO-MRM_5_Htp_100mg_30_Chewable_Tablets_Mrm, May 28, 2008, 2 Pages.
5 Htp 100mg 30 Chewable Tables Mrm—http://www.shopping.conn/xPF-MRM_5_Htp_100mg_30_Chewalbe_Tables_Mrm, Jun. 5, 2008, 3 Pages.
African Plant May Help Fight Fat, Lesley Stahl Reports on Newest Weapon in War on Obesity, Nov. 21, 2004, http://www.cbsnews.com/stories,2004/11/18/60minutes/main656458.shtml, Sep. 16, 2008, 2 Pages.
Beckman H. et al.—DL-phenylalanine versus imipramine: a double-blind controlled study, http://biopsychiarty.com/dl-phenylalanine.html. Sep. 16, 2008, 2 Pages.
Ray Sahelian, M.D.—GABA Supplement Information—Does GAB Work for Anxiety or Stress Reduction?, http://www.raysahelian.com/gaba.html, Sep. 16, 2008, 9 Pages.
Global-Nutrition-Inc.com—GABA Supplement Information, http://www.zhion.com/herb/Gymnema.html, Sep. 16, 2008, 2 Pages.
ZHION.COM—Gymnema Sylvestre Benefits and Side Effects, http://www.zhioin.com/herb/Gymnema.html, 4 Pages, Sep. 16, 2008.
Lifestyle Essentials—Hoodia, http://www.trueessentials.net/hoodia.asp, Jun. 3, 2008, 2 Pages.
Lifestyle Essentials—Hoodia 60 chewable tables per bottle, 2 Pages, Sep. 16, 2008.
Source Naturals—Hoodia Complex With Thermogenic Herbs, http://www.sourcenaturals.com/products/GP1833, Jun. 3, 2008, 2 Pages.
Hoodia Gordonii RESEARCH.ORG—Hoodia Gordonii: Natural Health Hoodia 57 Information, http://www.hoodiagordoniiresearch.org/, Sep. 16, 2008, 1 Page.
From Wikipedia—Phenylalanine, http://en.wikipedia.org/wiki/Phenylalanine, Sep. 16, 2008, 3 Pages.
Source Naturals—Source Naturals Introduces Hoodia Complex With Thermogenic Herbs, Rev. 1—Mar. 22, 2007, 1 Page.
WiseGEEK—What is Gymnema Sylvestre? http://www.wisegeet.com/what-is-gymnema-sylvestre.htm, Sep. 16, 2008, 2 Pages.

* cited by examiner

*Primary Examiner* — Christopher R Tate
(74) *Attorney, Agent, or Firm* — Sheppard, Mullin, Richter & Hampton LLP

(57) ABSTRACT

A chewable appetite suppressant composition includes a *Hoodia* extract, a 5-hydroxytryptophan, a *Gymnema Sylvestre*, and at least one amino acid derivative. The chewable appetite suppressant composition may further include flavorants.

14 Claims, No Drawings

APPETITE SUPPRESSANT COMPOSITION

BACKGROUND

1. Technical Field

One aspect of the present invention relates to an appetite suppressant composition. Another aspect of the present invention relates to a method of using an appetite suppressant tablet composition.

2. Background Art

Many appetite suppressant formulations are known. See, for example, U.S. Pat. App. Pub. No. 2005/0276839; PCT Pub. No. WO/2007/132479; U.S. Pat. App. Pub. 2006/0062859 and U.S. Pat. App. Pub. No. 2007/0292501.

SUMMARY

According to one embodiment, a chewable appetite suppressant composition is disclosed. This composition includes a *Hoodia* extract in an amount from about 10 to about 250 mg/total mg; a 5-hydroxytryptophan in an amount from about 10 to about 250 mg/total mg; a *Gymnema Sylvestre* extract in an amount from about 10 to about 250 mg/total mg; and at least one amino acid derivative.

In another embodiment, a chewable appetite suppressant composition is disclosed. This composition includes a *Hoodia* extract in an amount from about 10 to about 250 mg/total mg; a DL-phenylalanine in an amount from about 10 to about 500 mg/total mg; a gamma-aminobutyric acid in an amount from about 10 to about 250 mg/total mg; a 5-hydroxytryptophan in an amount from about 10 to about 250 mg/total mg; and a *Gymnema Sylvestre* extract in an amount from about 10 to about 250 mg/total mg.

In yet another embodiment, a chewable appetite suppressant tablet is disclosed. The tablet includes a *Hoodia* extract in an amount from about 10 to about 250 mg; a 5-hydroxytryptophan in an amount from about 10 to about 250 mg; a *Gymnema Sylvestre* extract in an amount from about 10 to about 250 mg; and at least one amino acid derivative.

DETAILED DESCRIPTION OF EMBODIMENTS

Where not expressly indicated, all numerical quantities in this description indicating amounts of material or conditions of reaction and/or use are to be understood as modified by the word "about" in describing the broadest scope of the present invention. Practice within the numerical limits stated is generally preferred.

The description of a single material, compound or constituent or a group or class of materials, compounds or constituents as suitable for a given purpose in connection with the present invention implies that mixtures of any two or more single materials, compounds or constituents and/or groups or classes of materials, compounds or constituents are also suitable. Also, unless expressly stated to the contrary, percent, "parts of," and ratio values are by weight. Description of constituents in chemical terms refers to the constituents at the time of addition to any combination specified in the description, and does not necessarily preclude chemical interactions among constituents of the mixture once mixed. The first definition of an acronym or other abbreviation applies to all subsequent uses herein of the same abbreviation and applies mutatis mutandis to normal grammatical variations of the initially defined abbreviation. Unless expressly stated to the contrary, measurement of a property is determined by the same technique as previously or later referenced for the same property.

Many appetite suppression formulations are known. For example, U.S. Pat. App. Pub. No. 2005/0276839 discloses an appetite satiation and hydration beverage. This document discloses an appetite satiation and hydration beverage that may optionally include *Hoodia*, DL-Phenylalanine, *Gymnema* extract, sucrose, malic acid, Acesulfame potassium, and sucralose. The document also mentions the addition of "amino acids" to the beverage formulation. The disclosure does not include the inclusion of either 5-HTP or GABA in the beverage formulation. Additionally, the disclosure is limited to beverage formulations, and does not extend to chewable formulations.

As another example, PCT Pub. No. WO/2007/132479 discloses a diet supplement for causing rapid weight loss and controlling appetite. The supplement composition includes at least one higher aliphatic alcohol and an extract of *Griffonia Simplicifolia* (5-HTP source). The dietary/nutritional supplement may include a combination of *Griffonia Simplicifolia*, *Gymnema sylvestre* leaf extract, *Hoodia*, along with other additives. According to this reference, the diet supplement may be delivered as a powder beverage mix, a liquid beverage, a lozenge, a pastille, a capsule, a tablet, a caplet or as a dietary gel.

U.S. Pat. App. Pub. 2006/0062859 discloses a composition and method to optimize and customize nutritional supplement formulations. The disclosure teaches the development of a weight management nutraceutical that comprises 5-HTP, *Gymnema*, *Hoodia*, DL-phenylalanine, and GABA. This document does not disclose a chewable tablet.

U.S. Pat. App. Pub. No. 2007/0292501 discloses a chewable soft gelatin capsule containing active ingredients of *Hoodia* and *Gymnema*, and additionally flavorings. This reference discloses a gelatin capsule formulation. These references also disclose a capsule including *Hoodia* and *Gymnema* for the purpose of appetite suppression. This reference also discloses an embodiment in which amino acids are a possible active ingredient, but does not disclose 5-HTP.

One or more embodiments of the present invention relate to chewable appetite suppressant tablets. In one or more embodiments, the chewable appetite suppressant tablet composition includes an extract of a plant of the genus *Hoodia* in an amount from about 10 to about 250 mg/tablet, 5-hydroxytryptophan ("5-HTP") in an amount from about 10 to about 250 mg/tablet, an extract of *Gymnema Sylvestre* in an amount from about 10 to about 250 mg/tablet, and at least one amino acid derivative.

In one or more embodiments, the chewable appetite suppressant tablet at least partially controls sugar craving by reducing the ability of the user's taste buds to sense sweet-tasting food products for a period of time, such as 60 minutes. Cravings may 5 last about 12 to 20 minutes according to certain embodiments, while many users do not effectively taste sweets for about 30 to 60 minutes, thereby allowing the craving to subside. During the 30 to 60 minute period, one or more of the active ingredients of the appetite suppressant tablet cause the user's mood to elevate and/or curbs hunger, thereby lessening the feelings of sadness, loneliness and/or boredom associated with sweet cravings. The user may regain control over a sweet craving because of the lack sensory feedback achieved by tasting and consuming sweet-tasting food products during the effective period of time. The chewable appetite suppressant tablets of one or more embodiments may supplement a user's dieting plans so as to reduce sugar cravings, which is a typical gateway for the consumption of sweet-tasting foods that may limit the success of dieting. In one embodiment, 1-3 tables may be consumed daily. The chewable form of the appetite suppressant eases delivery to the taste buds of the user. In one or more embodiments, the chewable appetite suppressant also acts as a mood elevator, which may help alleviate anxiety and moodiness that may be experienced during dieting.

The appetite suppressant tablet may include an extract of a plant of the genus *Hoodia*. In one or more embodiments, *Hoodia* is extracted from a cactus indigenous to South Africa. *Hoodia* extract includes one or more saponin compositions that interact directly with the brain's appetite system to suppress a user's food intake cravings. *Hoodia* extract is available from AHD International, Inc. of Atlanta, Ga.

In one embodiment, the *Hoodia* extract comprises 125 mg/tablet. In another embodiment, the *Hoodia* extract comprises 10 to 250 mg/tablet. In other embodiments, the *Hoodia* extract comprises 100 to 150 mg/tablet. In other embodiments, the *Hoodia* extract comprises 5 to 10 weight percent mg/tablet.

The appetite suppressant tablet may also include 5-hydroxytryptophan, otherwise referred to herein as 5-HTP. 5-HTP is an amino acid precursor to serotonin, which is a chemical residing within the human brain. Serotonin is a chemical responsible for the neurotransmission of happy feelings, and also acts to reduce hunger.

In one embodiment, 5-HTP comprises 50 mg/tablet. In another 5 embodiment, the 5-HTP comprises 10 to 250 mg/tablet. In other embodiments, 5-HTP comprises 40 to 60 mg/tablet. In other embodiments, 5-HTP comprises 5 to 25 mg/tablet.

The appetite suppressant tablet may include an extract of *Gymnema Sylvestre*. In one embodiment, the extract includes 75% by weight of *Gymnema Sylvestre*. *Gymnema Sylvestre* is an ayurvedic herb that substantially reduces the sense of sweet taste for a period of time, such as 60 minutes, after oral administration. *Gymnema Sylvestre* also functions to help balance blood sugar, which may reduce sugar cravings caused by hyperglycemia.

In one embodiment, the extract of *Gymnema Sylvestre* comprises 50 mg/tablet. In another embodiment, the extract of *Gymnema Sylvestre* comprises 10 to 250 mg/tablet. In other embodiments, the extract of *Gymnema Sylvestre* comprises 40 to 60 mg/tablet. In other embodiments, the extract of *Gymnema Sylvestre* comprises 5 to 25 mg/tablet.

The appetite suppressant tablet may include at least one amino acid derivative. The at least one amino acid derivate acts as a calming agent within the brain and helps reduce appetite. Amino acid derivatives may also reduce stress, which may cause overeating. In one or more embodiments, the at least one amino acid derivative includes gamma-aminobutyric acid, otherwise referred to as GABA. GABA is a widespread inhibitory neurotransmitter in the brain.

In one embodiment, the at least one amino acid derivative comprises 75 mg/tablet. In another embodiment, the at least one amino acid derivative comprises 10 to 250 mg/tablet. In other embodiments, the at least one amino acid derivative comprises 60 to 90 mg/tablet. In other embodiments, the at least one amino acid derivative comprises 5 to 25 mg/tablet.

The appetite suppressant tablet may include DL-Phenylalanine, which is an amino acid with appetite suppression and anti-depressant effects. DL-Phenylalanine also acts as a pain killer.

In one embodiment, DL-Phenylalanine comprises 100 mg/tablet. In another embodiment, DL-Phenylalanine comprises 10 to 500 mg/tablet. In other embodiments, DL-Phenylalanine comprises 80 to 120 mg/tablet. In other embodiments, the DL-Phenylalanine comprises 10 to 25 mg/tablet.

In one embodiment, the appetite suppressant tablet may also include a bitter blocker, such as bitter blocker Frutarom 916794. The bitter blocker may mask the bitter taste of one or more of the ingredients of the appetite suppressant tablet and/or the bitter taste that may result from consuming a food after oral administration of the appetite suppressant tablet.

In one embodiment, the bitter blocker comprises 5 mg/tablet. In another embodiment, the bitter blocker comprises 1 to 100 mg/tablet. In other embodiments, the bitter blocker comprises 1 to 10 mg/tablet. In other embodiments, the bitter blocker comprises 4 to 6 mg/tablet.

In one or more embodiments, the appetite suppressant tablet may include one or more flavorants, such as fruit flavorants. Non-limiting examples of fruit flavorants include pomegranate, lemon, lime, mint and spearmint. The one or more flavorants may mask the unpleasant or bitter taste of one or more of the ingredients of the appetite suppressant tablet and/or the bitter taste that may result from consuming a food after oral administration of the appetite suppressant tablet.

In one embodiment, the one or more flavorants comprise 500 mg/tablet. In another embodiment, the one or more flavorants comprises 100 to 1000 mg/tablet. In other embodiments, the one or more flavorants comprise 400 to 600 mg/tablet. In other embodiments, the one or more flavorants comprise 10 to 200 mg/tablet.

The compositions of one or more embodiments are made by introducing a combination of the active ingredients set forth above and in the examples with a suitable number of inactive ingredients. Examples 1 and 2 set forth below provide a combination of active and inactive ingredients brought together to obtain appetite suppressant tablets according to one or more embodiments.

EXAMPLE 1

A chewable appetite suppressant tablet for decreasing the sugar cravings in an individual, e.g., a human being, is provided. Table 1 lists the active ingredients for the chewable appetite suppressant of Example 1.

TABLE 1

| Active Ingredient | mg/tablet |
|---|---|
| Compressible sucrose | 1500 |
| FPI N&A pomegranate/lemonade #6021G (flavorant) | 500 |
| Hoodia | 125 |
| Red 40 lake or Beet juice powder | 100 |
| DL-phenylalanine | 100 |
| Malic acid (flavorant) | 75 |
| GABA | 75 |
| 5-HTP | 50 |
| Gymnema | 50 |
| Acesulfame K | 20 |
| Sucralose | 10 |
| Stearic acid | 10 |
| Bitter Blocker Frutarom 916794 | 5 |
| TOTAL | 2620 |

The combination of active and inactive ingredients are mixed and pressed together using one or more known tablet manufacturing processes.

EXAMPLE 2

A chewable appetite suppressant tablet for decreasing the sugar cravings in an individual, e.g., a human being, is provided. Table 2 lists the active ingredients for the chewable appetite suppressant of Example 2.

TABLE 2

| Active Ingredient | mg/tablet |
| --- | --- |
| Compressible Sucrose | 1500 |
| FPI Wintergreen, 7300G | 500 |
| FPI Mint, 1893G | 200 |
| Hoodia | 125 |
| DL Phenylalanine | 100 |
| GABA | 75 |
| 5-HTP | 50 |
| Gymnema 75% | 50 |
| Acesulfame K | 20 |
| Sucralose | 10 |
| Stearic acid | 10 |
| Bitter Blocker Frutarom 9166794 | 5 |
| TOTAL | 2645 |

The combination of active and inactive ingredients are mixed and pressed together using one or more known tablet manufacturing processes.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A chewable appetite suppressant composition comprising:
   a *Hoodia* extract in an amount from about 10 to about 250 mg/total mg;
   5-hydroxytryptophan in an amount from 40 to 60 mg/total mg;
   a *Gymnema Sylvestre* extract in an amount from about 10 to about 250 mg/total mg; and
   at least one amino acid derivative.

2. The chewable appetite suppressant composition of claim 1, wherein the at least one amino acid derivative is gamma-aminobutyric acid present in an amount from about 10 to about 250 mg/total mg.

3. The chewable appetite suppressant composition of claim 2, further comprising a bitter blocker.

4. The chewable appetite suppressant composition of claim 1, wherein the *Hoodia* extract is present in an amount of from about 100 to about 150 mg/total mg.

5. The chewable appetite suppressant composition of claim 1, wherein the *Gymnema Sylvestre* extract is present in an amount of from about 40 to about 60 mg/total mg.

6. The chewable appetite suppressant composition of claim 1, further comprising at least one flavorant.

7. The chewable appetite suppressant composition of claim 1, further comprising DL-phenylalanine in an amount of from about 80 to 120 mg/total mg.

8. The chewable appetite suppressant composition of claim 1 as a tablet.

9. A chewable appetite suppressant composition comprising:
   a *Hoodia* extract in an amount from about 10 to about 250 mg/total mg;
   DL-phenylalanine in an amount from about 10 to about 500 mg/total mg;
   gamma-aminobutyric acid in an amount from about 10 to about 250 mg/total mg;
   5-hydroxytryptophan in an amount from 40 to 60 mg/total mg; and
   a *Gymnema Sylvestre* extract in an amount from about 10 to about 250 mg/total mg.

10. The chewable appetite suppressant composition of claim 9, wherein the *Gymnema Sylvestre* extract is present in an amount of from about 40 to about 60 mg/total mg.

11. The chewable appetite suppressant composition of claim 9, wherein the DL-phenylalanine is present in an amount of from about 80 to about 120 mg/total mg.

12. The chewable appetite suppressant composition of claim 9, wherein the *Hoodia* extract is present in an amount of from about 100 to about 150 mg/total mg.

13. The chewable appetite suppressant composition of claim 9, further comprising a bitter blocker.

14. A chewable composition comprising:
   a *Hoodia* extract in an amount from about 100 to about 150 mg/total mg;
   5-hydroxytryptophan in an amount from 40 to 60 mg/total mg;
   *Gymnema Sylvestre* extract in an amount from about 10 to about 250 mg/total mg;
   gamma-aminobutyric acid present in an amount from about 10 to about 250 mg/total mg; and
   DL-phenylalaine in an amount of from about 80 to 120 mg/total mg.

* * * * *